US006961405B2

United States Patent
Scherch

(10) Patent No.: US 6,961,405 B2
(45) Date of Patent: Nov. 1, 2005

(54) METHOD AND APPARATUS FOR TARGET POSITION VERIFICATION

(75) Inventor: John David Scherch, Pittsburgh, PA (US)

(73) Assignee: Nomos Corporation, Cranberry Township, PA (US)

( * ) Notice: Subject to any disclaimer, the term of this patent is extended or adjusted under 35 U.S.C. 154(b) by 136 days.

(21) Appl. No.: 10/680,327

(22) Filed: Oct. 7, 2003

(65) Prior Publication Data
US 2005/0020917 A1 Jan. 27, 2005

Related U.S. Application Data
(60) Provisional application No. 60/416,635, filed on Oct. 7, 2002.

(51) Int. Cl.[7] .............................. A61B 5/01; A61B 5/10; A61B 17/00; A61B 8/00; A61N 5/10
(52) U.S. Cl. ....................................................... 378/65
(58) Field of Search ........................... 455/445; 378/65, 378/150; 600/439; 128/897, 916

(56) References Cited
U.S. PATENT DOCUMENTS

| | | |
|---|---|---|
| 5,411,026 A | 5/1995 | Carol |
| 5,596,619 A | 1/1997 | Carol |
| 5,622,187 A | 4/1997 | Carol |
| 5,802,136 A | 9/1998 | Carol |
| 6,038,283 A | 3/2000 | Carol et al. |
| 6,325,758 B1 | 12/2001 | Carol et al. |
| 6,393,096 B1 | 5/2002 | Carol et al. |

Primary Examiner—William D. Cumming
(74) Attorney, Agent, or Firm—Bracewell & Giuliani LLP

(57) ABSTRACT

A system and method for aligning the position of a target within a body of a patient to a predetermined position used in the development of a radiation treatment plan can include an ultrasound probe used for generating live ultrasound images, a position sensing system for indicating the position of the ultrasound probe with respect to the radiation therapy device, and a computer system. The computer system is used to display the live ultrasound images of a target in association with representations of the radiation treatment plan, to align the displayed representations of the radiation treatment plan with the displayed live ultrasound images, to capture and store at least two two-dimensional ultrasound images of the target overlaid with the aligned representations of the treatment plan data, and to determine the difference between the location of the target in the ultrasound images and the location of the target in the representations of the radiation treatment plan.

25 Claims, 7 Drawing Sheets

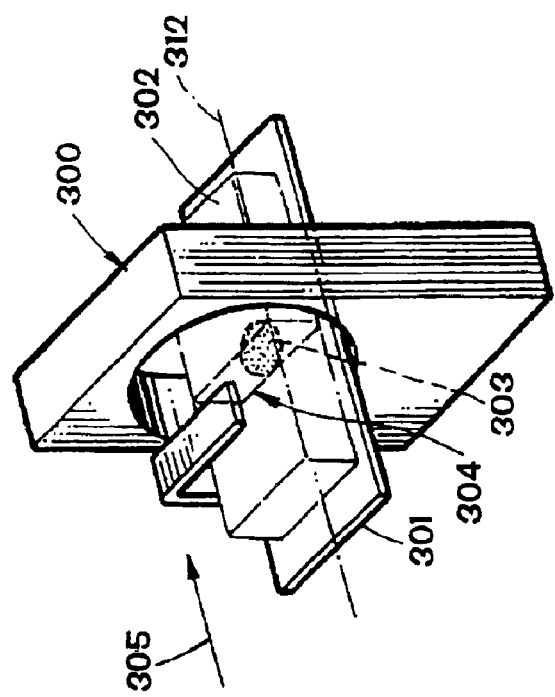
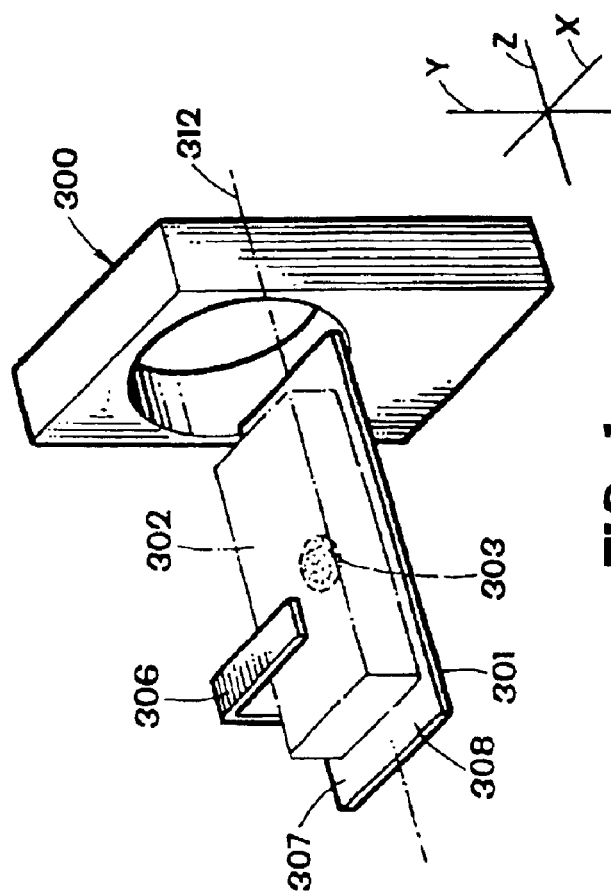
FIG. 1
(PRIOR ART)
FIG. 2
(PRIOR ART)

METHOD AND APPARATUS FOR TARGET POSITION VERIFICATION

RELATED APPLICATION

This application claims the benefit of U.S. Provisional Patent Application Ser. No. 60/416,635, titled "Method And Apparatus For Target Position Verification," filed Oct. 7, 2002.

BACKGROUND OF THE INVENTION

1. Field of the Invention

The invention relates to a method and apparatus for verifying and aligning the position of a target to be treated by a radiation therapy device operating in accordance with a radiation therapy plan.

2. Description of the Related Art

Modern day radiation therapy of cancerous tumors has two goals: eradication of the tumor and avoidance of damage to healthy tissue and organs present near the tumor. It is believed that a vast majority of tumors can be eradicated completely if a sufficient radiation dose is delivered to the tumor volume; however, complications may result from use of the necessary effective radiation dose, due to damage to healthy tissue which surrounds the tumor, or to other healthy body organs located close to the tumor. The goal of radiation therapy is to confine the delivered radiation dose to only the tumor volume defined by the outer surface of the tumor, while minimizing the dose of radiation to surrounding healthy tissue or adjacent healthy organs or structures.

Radiation therapy treatment typically uses a radiation delivery device such as a linear accelerator, or other radiation producing source, to treat the tumor. The radiation delivery device typically has a radiation beam source which is positioned about the patient and directs the radiation beam toward the tumor to be treated. Various types of devices have been proposed to conform the shape of the radiation treatment beam to follow the spatial contour of the tumor as seen by the radiation treatment beam, from a linear accelerator, as it passes through the patient's body into the tumor, during rotation of the radiation beam source, which is mounted on a rotatable gantry of the linear accelerator. Multileaf collimators, which have multiple leaf, or finger, projections which can be moved individually into and out of the path of the radiation beam, can be so programmed, and are examples of such devices. Various types of radiation treatment planning systems can create a radiation treatment plan, which when implemented will deliver a specified dose of radiation shaped to conform to the target, or tumor, volume, while limiting the radiation dose delivered to sensitive surrounding healthy tissue or adjacent healthy organs or structures.

A basic problem in radiation therapy is knowing where the target, or tumor, is located at the time the radiation therapy treatment is occurring. The use of the term "target" is intended to include not only a tumor or a body organ, or portion thereof, to be treated, but also an organ, sensitive body structure, or portion thereof to be avoided in the radiation therapy treatment. It is assumed that the patient's position and the target's position within the patient will be grossly, or nominally, the same at the time of radiation treatment, as it was at the time the radiation treatment plan was created. If the position of the target is not the same as it was at the time the treatment plan was determined, the dose of radiation may not be delivered to the correct location within the patient's body. Since patients are not always positioned properly on the treatment table of the radiation therapy device, which may be a linear accelerator or a cobalt unit, and since organs of a patient may move within the patient from day to day, the target may not be positioned at the exact location where the radiation therapy plan has assumed it would be located. Thus, present day radiation therapy plans typically regard the target to be treated to occupy a space in the patient's body which is larger than it really occupies, in order to insure that the target to be treated regardless of its location within the patient's body, falls within the volume of tissue which receives the desired radiation treatment dose.

A disadvantage of such conventional radiation therapy plans is that there is a major concern associated with increasing the volume of tissue which is treated, to insure that the actual target to be treated receives the desired dose of radiation. Because some healthy tissue surrounds the target to be treated, or healthy organs, or sensitive structures, lie adjacent to the target to be treated, delivering the maximum desired radiation dose to this larger volume of tissue may occur and increase risk of damaging healthy tissue, healthy organs, or sensitive structures. Due to this increased risk, some Oncologists will deliver a smaller radiation dose to the larger treatment volume, which is safer for the healthy tissue, with the potential disadvantage of underdosing the target to be treated.

Thus, the art has sought a method and apparatus for verifying the position of a target, within a body of a patient, to determine if it will conform to its desired position which has been used in the development of the radiation treatment plan and to allow for an alignment of the target with the desired position when not in such position in order to prevent healthy tissue surrounding the target, or healthy organs and sensitive structures from being exposed to an undesired amount of radiation. Ultrasound has been proposed to try to satisfy that which the art has sought. However, ultrasound has some significant image capture limitations.

When a user uses an ultrasound probe to locate an object of interest, a key component in the process is that the image they are seeing is dynamic, changing in real time and in direct correlation to how the individual manipulates the probe. The ultrasound image itself is by its nature grainy, and it is very common for it to be difficult, especially for the less than expert user, to identify information from a static image. Generally, the user, or sonographer, continuously moves the ultrasound probe throughout a procedure, to create a dynamic sequence of images which the sonographer may then mentally integrate into a true three-dimensional image of the object. The sonographer may settle on a specific image to measure, or communicate to others what the sonographer sees in the image, but the sonographer inevitably returns to a dynamic mode to get his/her bearings and to further his/her search. For example, any parent who has had a chance to see an ultrasound procedure of their unborn baby finds the baby is easy to pick out and view because of how it moves, and how the operator moves/manipulates the image. In contrast, when the sonographer captures a still, or static, image for them to take home and show the family, it is often impossible to identify the features in the still, or static, image that were so obvious in the live, or dynamic image.

A method and apparatus which implements ultrasound in target, or tumor position verification is described in U.S. Pat. No. 6,325,758, by Carol et al., entitled "Method and Apparatus for Target Position Verification," issued Dec. 4, 2001, and commonly assigned to the assignee of the present invention, and incorporated by reference.

For a variety of reasons, use of static ultrasound images may not be as easy to use when compared to viewing the live, dynamic ultrasound. It may be that information that the user could use to identify the target may come from the changes in the ultrasound image from moment to moment, as the user manipulates the ultrasound probe. Therefore, the art has sought a system and method for treating a target within a body of a patient and for aligning a position of the target within the body of the patient to a predetermined position used in the development of the radiation treatment plan when not in such position that thereby allows for performing the alignment process directly upon the live, dynamic ultrasound image.

SUMMARY OF THE INVENTION

In accordance with the invention, the foregoing advantages have been achieved through the present target alignment system for use by a user with a radiation therapy device and a radiation treatment plan for treating a target within a body of a patient and for aligning a position of the target within the body of the patient to a predetermined position used in the development of the radiation treatment plan. An embodiment of the present invention includes an ultrasound probe for generating live ultrasound images of the target, a position sensing system preferably including a 3-D digitizer articulated arm for indicating the position of the ultrasound probe with respect to the radiation therapy device, adapted to provide a reference location of the target with respect to the radiation therapy device, and a computer system including a computer having memory and a monitor with a screen associated therewith, and a radiation treatment plan stored in the memory.

The computer is responsive to the position sensing system and ultrasound probe and is adapted to display on the monitor screen the live ultrasound images of the target in association with representations of the radiation treatment plan. These overlaid representations can include an isodose distribution contour and a structure contour which are adjusted relative to the displayed live ultrasound image as the angle of the ultrasound probe is changed relative to a patient's anatomy. More specifically, the computer recalculates dose and structure contour data such that the contours displayed are for a volume slice of radiation treatment plan data that is coincident with a current plane of the live ultrasound image.

The computer advantageously is further adapted to align the displayed representations of the radiation treatment plan with the displayed live ultrasound images in response to a user input. In an embodiment of the present invention, the computer system responds to the user touching a monitor screen display anywhere within boundaries of the live ultrasound image displayed on the monitor screen and dragging a user finger in a desired direction to move the position of the contours relative to the live ultrasound image, whereby the displayed contours exhibit identical spatial displacements relative to each other. The computer is further adapted to capture and store at least two two-dimensional ultrasound images of the target overlaid with the aligned representations of the treatment plan data, each disposed in a different geometric orientation.

The computer system is further adapted to determine, in response to the alignment, the difference between the location of the target in the ultrasound images and the location of the target in the representations of the radiation treatment plan, and to display geometric information concerning such difference upon capture of two two-dimensional images.

In an embodiment of the present invention, the computer is adapted to display an image capture screen having a live ultrasound image window for displaying a live ultrasound image overlaid with position adjustable representations of the radiation treatment plan. The position of the representations of the radiation treatment plan are displayed relative to a current plane of the displayed live ultrasound image for performing a user alignment of the displayed representations of the radiation treatment plan with respect to the displayed live ultrasound image, and at least two other static image windows displaying at least two captured two-dimensional ultrasound images of the target overlaid with the corresponding aligned representations of the radiation treatment plan The foregoing advantages have also been achieved through a method of aligning the position of a target within a body of a patient to a predetermined position used in the development of a radiation treatment plan for the patient. The method includes disposing the patient on a treatment table of a radiation therapy device, providing an ultrasound probe, manipulating the ultrasound probe to display live ultrasound images of the target, and displaying spatially associated representations of the radiation treatment plan, preferably in the form of dose and structure contours, and overlaid upon the live ultrasound image. As the user adjusts the position an angle of the ultrasound probe relative to the patient's anatomy, features of the live ultrasound image overlaid with associated dose and structure contour data are tracked. More specifically, as ultrasound probe is moved, dose and structure contour data is recalculated such that the contours displayed are for the volume slice of the radiation treatment plan that is coincident with the current plane of the live ultrasound image.

The method also includes aligning the displayed representations of the radiation treatment plan with the displayed live ultrasound images. The user performs a virtual alignment by moving the contours overlaid on the live ultrasound image device until they are correctly aligned to the patient anatomy as viewed with respect to the live ultrasound image. This movement is preferably accomplished by touching a monitor screen display anywhere within the boundaries of the live ultrasound image and dragging a finger in a desired direction. Advantageously, the computer regenerates at periodic intervals the displayed contours as overlaid upon the live ultrasound image, such that they appear to track the motion of the finger.

The method also includes capturing at least two two-dimensional ultrasound images of the target in the patient's body overlaid with the aligned representations of the radiation treatment plan data, the ultrasound probe being disposed in a different geometric orientation for each captured ultrasound image. The alignment and the following capture of the ultrasound images accomplished to determine an amount, and type, of movement of at least one of the treatment table, the radiation therapy device, and the patient required to position the target to conform the current position of the target to the position of the target used in the development of the radiation treatment plan.

The target alignment system and methods have the advantages of preventing healthy tissue surrounding the tumor, or healthy organs or sensitive structures located adjacent the tumor, from being exposed to an undesired amount of radiation, and permits the verification that the target with respect to the radiation therapy treatment device conforms to the desired position of the target in the radiation treatment plan, and, if not, adjustment of the position thereof.

BRIEF DESCRIPTION OF THE DRAWINGS

FIG. 1 is a perspective view of a conventional imaging device with a patient schematically illustrated on the imaging table, the patient having a target disposed within the patient's body;

FIG. 2 is a perspective view of the imaging device of FIG. 1, with the patient passing through the imaging device;

Figure 4:
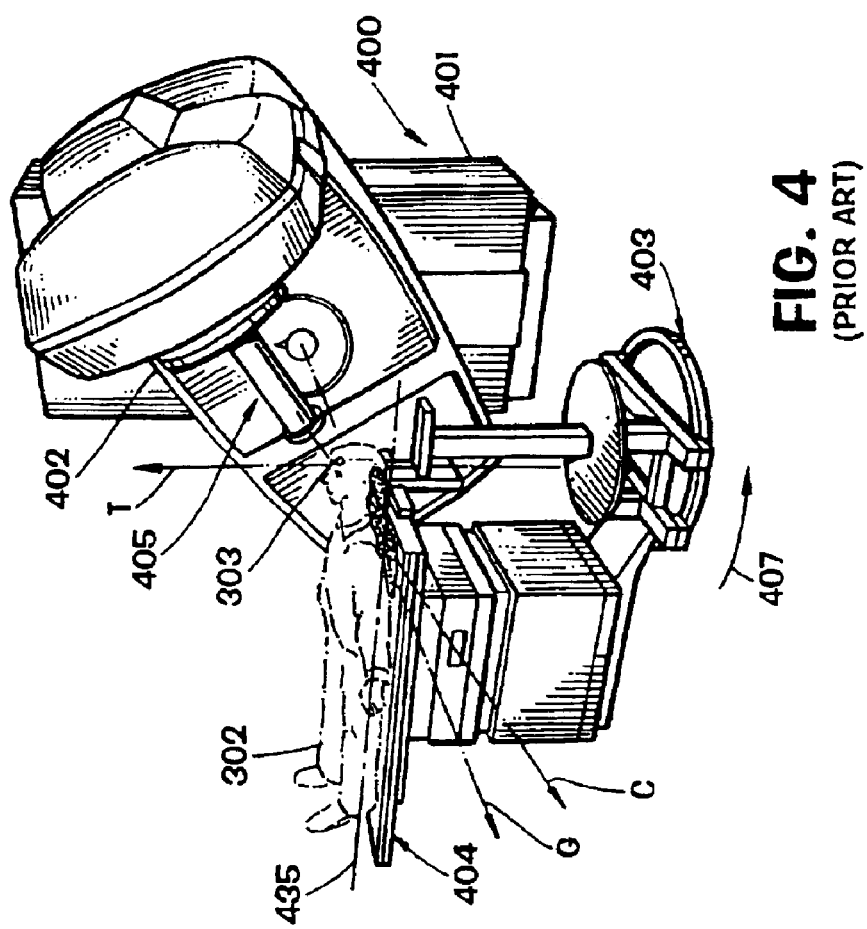
FIG. 4 is a perspective view of a conventional radiation therapy device, or linear accelerator, including a rotatable couch, or treatment table, collimator, and gantry.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION

With reference to FIG. 1, a conventional imaging device 300 is schematically shown and includes a conventional imaging table 301, upon which is disposed a patient 302 having a tumor, or target, 303 within the patient's body 302. As previously discussed, the use of the term "target" throughout this specification, including the claims, includes, as appropriate, a tumor or an organ, or portion thereof, to be treated, or an organ, sensitive structure, or portion thereof, which is not to be treated in the radiation therapy plan. Imaging device 300 may be a computerized tomographic ("CT") scanning device, as illustrated in FIG. 1, or may alternatively be a magnetic resonance ("MR") imaging device, as are known in the art. CT scanning devices, such as imaging device 300, produce an image representing a "slice" of body tissue 304 (shown in phantom lines in FIG. 2), one such slice being illustrated in FIG. 3. A plurality of images, or diagnostic images, 304 are obtained by the imaging device 300, and this series of "slices", which constitute a complete CT study, represent a three-dimensional picture of a particular volume, or section, of the patient's body, such as that portion of the patient's body 302 which includes target 303 therein. The plurality of "slices", or diagnostic images, 304 are obtained by moving the patient 302, disposed upon imaging table 301, through imaging device 300 in the direction shown by arrow 305 as illustrated in FIG. 2.

If desired, as hereinafter described in greater detail, the orientation of the patient 302 upon imaging table 301 when the slices, or images, 304 are made, may be predetermined, or known, as by fixating the patient's body 302 to the imaging table 301 by use of a conventional fixation device 306. Fixation device 306, illustrated schematically in FIGS. 1 and 2, and as shown in the slice, or image 304, of FIG. 3, may be any conventional invasive, or noninvasive, fixation device which attaches to the patient 302 a coordinate system and secures the patient to the imaging table 301. Typically, the coordinate system is one which is forced by its attachment mechanism to be coplanar with the plane 307 in which lies the upper surface 308 of imaging table 301; however, any fixation device 306 having a coordinate system may be utilized provided the relationship between the coordinate system and the imaging table 301 is known, when it is desired to fixate patient 302.

Figure 3:
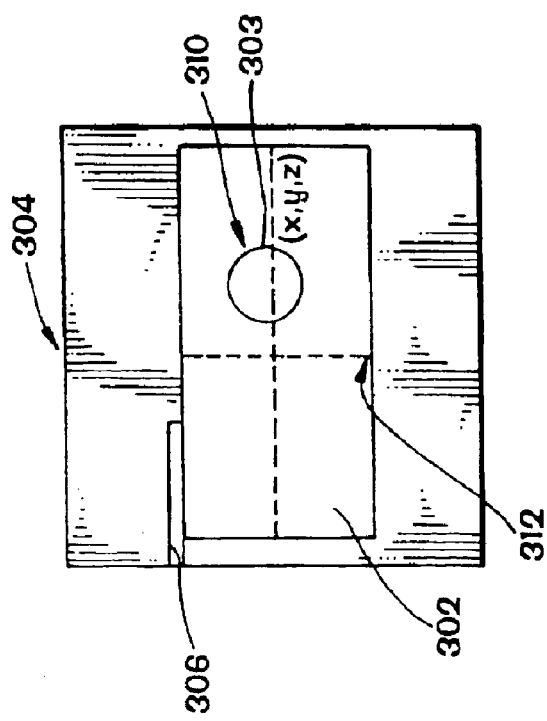
FIG. 3 is an example of an image produced by the imaging device of FIG. 1, illustrating the position of the target within the patient's body.

In FIG. 3, the target 303 is shown disposed within the patient's body 302 at a particular location having conventional X, Y, and Z coordinates, which are determined in a conventional manner by the CT scanner with respect to the frame of reference, or the coordinate system, of the imaging device as shown by its X, Y and Z axes in FIG. 1. The cross-sectional configuration of target 303 in FIG. 3 appears as circular, for illustrative purposes only.

After the series of slices, or images, 304 of the patient's body 302 which include target 303 therein, are obtained, the series of slices, or diagnostic images are then transferred in a conventional manner to a conventional radiation treatment planning system which includes conventional software to permit a physician to two-dimensionally outline the outer surface 310 of target 303 in each slice 304. The computer software of the radiation treatment planning system may also construct, or create, a three-dimensional rendering of the outer surface 310 of target 303 from the plurality of slices, or diagnostic images, 304. In the case of imaging device 300 of FIG. 1, its frame of reference is the longitudinal axis 312, or Z axis, of imaging table 301. In a conventional manner, a radiation treatment plan is generated by the radiation treatment planning system, whereby target 303 may receive the necessary radiation dose to properly treat target 303. The radiation treatment plan could be, if desired, a conformal radiation treatment plan, whereby the shape of the radiation beam will conform to the spacial contour, or outline, 310 of target 303 as seen by the radiation beam as it passes through the target 303, or the "beam's eye view" of the target 303 during rotation of the radiation beam source about the target 303.

With reference to FIG. 4, a conventional radiation treatment device 400, which is preferably a conventional linear accelerator 401, includes a gantry 402, turntable 403 which causes treatment table 404 to rotate therewith, and a collimator 405, which preferably is a collimator capable of conforming the shape of the radiation beam to conform to the beam's eye view of the target being treated. The three axes of rotation of the gantry 402, turntable and treatment table 403, 404 and collimator 405 are designated with the letters G, T, and C, respectively. For illustrative purposes only, the target 303 within patient's body 302 is disposed in the patient's head in FIG. 4; however, the method and apparatus of the present invention may be used with targets disposed anywhere in the patient's body, that can be seen by the imaging device 300. The target 303 which is treated by linear accelerator 401 is disposed at the isocenter of the linear accelerator 401. The isocenter 406 is defined as the point of intersection of the three axes of rotation, C, G, and T of linear accelerator 401. The previously described radiation treatment plan controls the operation of linear accelerator 401, and controls the operation of collimator 405, rotation of gantry 402, and location of treatment table 404, in a conventional manner. As previously discussed, the position and orientation of target 303 within patient's body 302 with respect to linear accelerator 401 may not necessarily be the same as the position and orientation of target 303 which was utilized in developing the radiation treatment plan. Thus, the present invention is used to verify that the position and orientation of target 303 within the patient's body 302 conforms, or matches, the position and orientation of the target 303 in the diagnostic slices 304 utilized in developing the radiation treatment plan.

Figure 5:
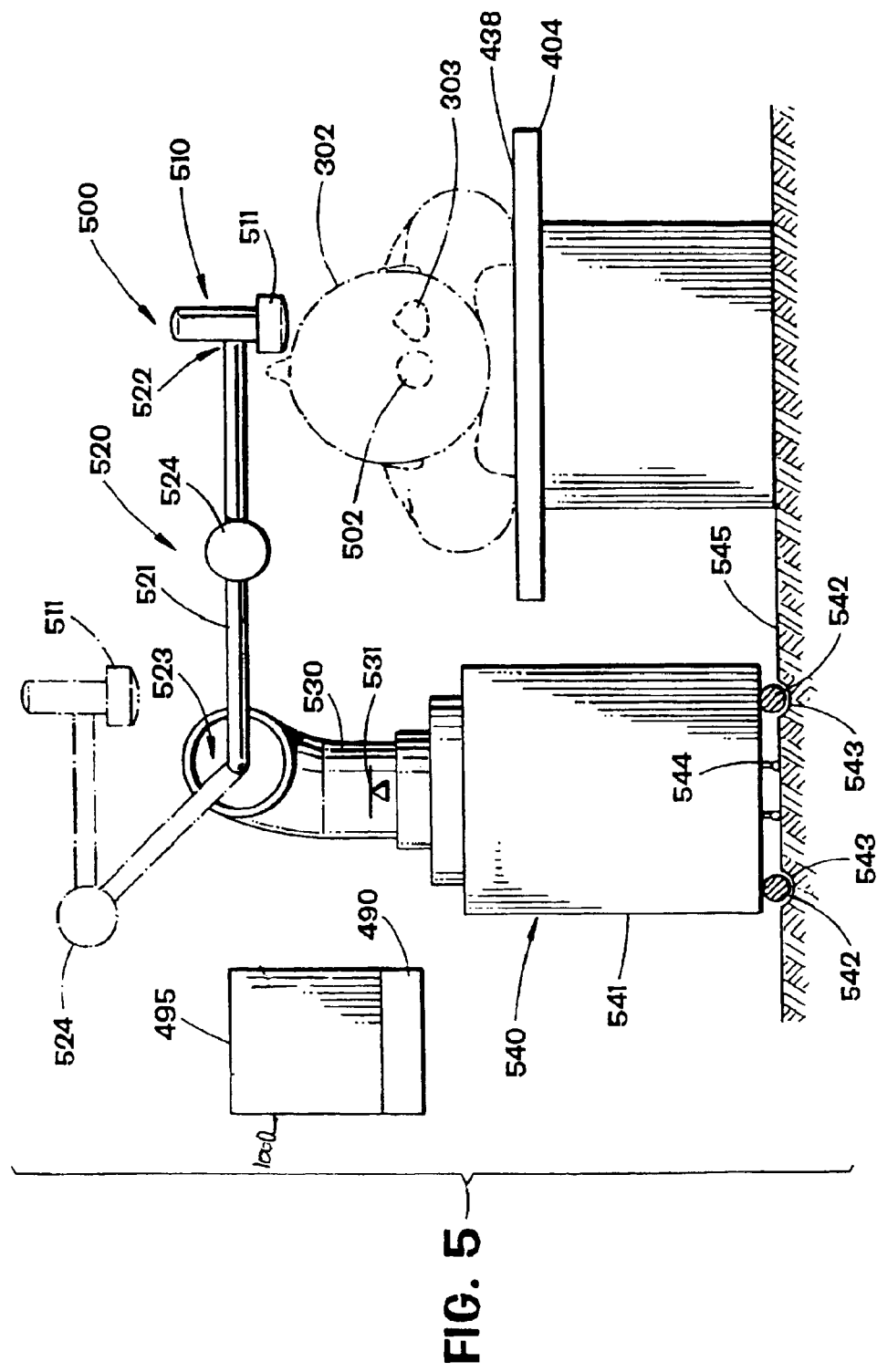
FIG. 5 is a side view of a target position verification system in accordance with the present invention, viewed along the longitudinal axis of treatment table of the radiation therapy device.

With reference to FIG. 5, patient 302 is disposed on treatment table 404, with patient 302 laying flat upon treatment table 404, although patient 302 may not be laying precisely in the same orientation with respect to treatment table 404, as patient 302 had when patient 302 was lying upon imaging table 301. Patient 302 is laying on the upper surface 438 of treatment table 404, with the patient's spinal cord 502 being disposed substantially parallel with the longitudinal axis 435 of treatment table 404. Although it might be desirable to immobilize patient 302 during the radiation therapy treatment, due to the prolonged time required for many treatments, the patient's orientation on the treatment table 404 need not be precisely the same as its orientation on imaging table 301; however patient 302 is preferably laying flat on treatment table 404. Since the orientation of the patient's body 302 is not the same as it was when the patient 302 was imaged by imaging device 300, it should be apparent that it is very likely the position and orientation of target 303 with respect to treatment table 404 and linear accelerator 401 will not conform, or match, the position and orientation of target 303 upon which the radiation treatment plan for linear accelerator 401 has been based. It is thus necessary to verify the position of target 303 to determine if it will conform to its desired position which has been used in the radiation treatment plan previously obtained. Further, it is necessary to determine where to relocate target 303 with respect to linear accelerator 401, so that the position and orientation of target 303 will conform to its position and orientation required by the radiation treatment plan.

Still with reference to FIG. 5, the target alignment system 500 of the present invention generally includes: a means for generating 510 ultrasound images or windows 705, 725, 735, 825, 835 (FIGS. 7–9) of the target 303; a position sensing system 520 for indicating the position of the generating means 510 with respect to the radiation therapy device 400 (FIG. 4), whereby the location of the target 303 with respect to the radiation therapy device is known; and a computer 490 having a monitor 495 associated therewith. For illustrative purposes only, target 303 in FIG. 5 is located in the patient's prostate. Preferably, the means for generating 510 the ultrasound image, such as 710, is an ultrasound image generator, such as an ultrasound probe 511 and may be a commercially available ultrasound probe 511, Model 4.5/50 from Diasonics Vingmed Ultrasound, Inc. of Santa Clara, Calif. Ultrasound probe 511 can generate two-dimensional ultrasound images of the portion of the patient's body 302 containing target 303, while patient 302 is on treatment table 404. Ultrasound probe 511 may be provided in any suitable manner as by attaching or mounting it to radiation therapy device 400, treatment table 404, gantry 402, or any other available location, provided the position sensing system, or means, 520, can determine the position of ultrasound probe 511 with respect to the radiation therapy device 400. Preferably, position sensing system 520 is a position sensor, such as a 3-D digitizer articulated arm 521. The 3-D digitizer articulated arm 521 is preferably a commercially available, model Microscribe 3DX, 3-D digitizer articulated arm 521 manufactured by Immersion Corporation of San Jose, Calif. Other types of position sensors could be utilized to determine the position of the ultrasound probe 511, or any other type of image generator which is utilized, as will be hereinafter discussed. Examples of such position sensors are: camera systems; retro reflectors; and laser positioning systems, among others.

Articulated arm 521 includes a plurality of sensors (not shown) which track the position and orientation of the first end 522 of arm 521 to which probe 511 is mounted. The output of the sensors in conjunction with computer 490, indicate the position of ultrasound probe 511 with respect to radiation therapy device 400. This position sensing system 520 tracks the position and orientation of the ultrasound probe 511. Position sensing systems other than articulated arm technology, such as 3-D digitizer articulated arm 521, may be used with ultrasound probe 511. Examples of other types of position sensing systems that may be used are those based on: triangulating directional microphones and spark gaps; video camera arrays; and magnetic field orientation.

While the first end 522 of 3-D digitizer articulated arm 521 is connected to ultrasound probe 511, a second end 523 of articulated arm 521 is associated with the base unit 530 which contains some of the circuitry and sensors for articulated arm 521. Base unit 530 also includes a tilt sensor 531 which can indicate if articulated arm is level with respect to gravity, in the event floor 545 is not exactly level, which in turn can also affect the angular disposition of the gantry 402. By use of the tilt sensor 531, the angular disposition of the cart 541, upon which the base unit 530 may be disposed, may be determined; and the angular disposition of the gantry 402 may also be determined, so that the articulated arm 521 may be, aligned, or oriented, to the radiation therapy device, as will be hereinafter described. Disposed between first and second ends 522, 523, is a joint member 524, which assists in articulation of the arm 521. As shown in phantom lines, the first end 522 of articulated arm 521 may be rotated about joint member 524 and the second end 523 of arm 521 can also rotate about base unit 530, as is conventional in the art. Appropriate software associated with 3-D digitizer articulated arm 521, in cooperation with computer 490, permits the operator of the target position verification system 500 to always know the position and orientation of ultrasound probe 511, as will be hereinafter described in greater detail.

Still with reference to FIG. 5, preferably the articulated arm 521 is mounted on a support 540 adjacent treatment table 404. Preferably, support 540 is a moveable support, or cart 541, disposed on a plurality of wheels 542. By mounting articulated arm 521, with its associated ultrasound probe 511 on a moveable support, or cart 541, the target position verification system 500 may be easily placed at its preferred location adjacent treatment table 404. It may also be readily moved away from treatment table 404 at the time the radiation therapy treatment is to begin, and may be conveniently moved and stored out of the way of the radiation therapy device 400. The base unit 530 is preferably firmly attached to the support member 540, or cart 541.

Figure 6:
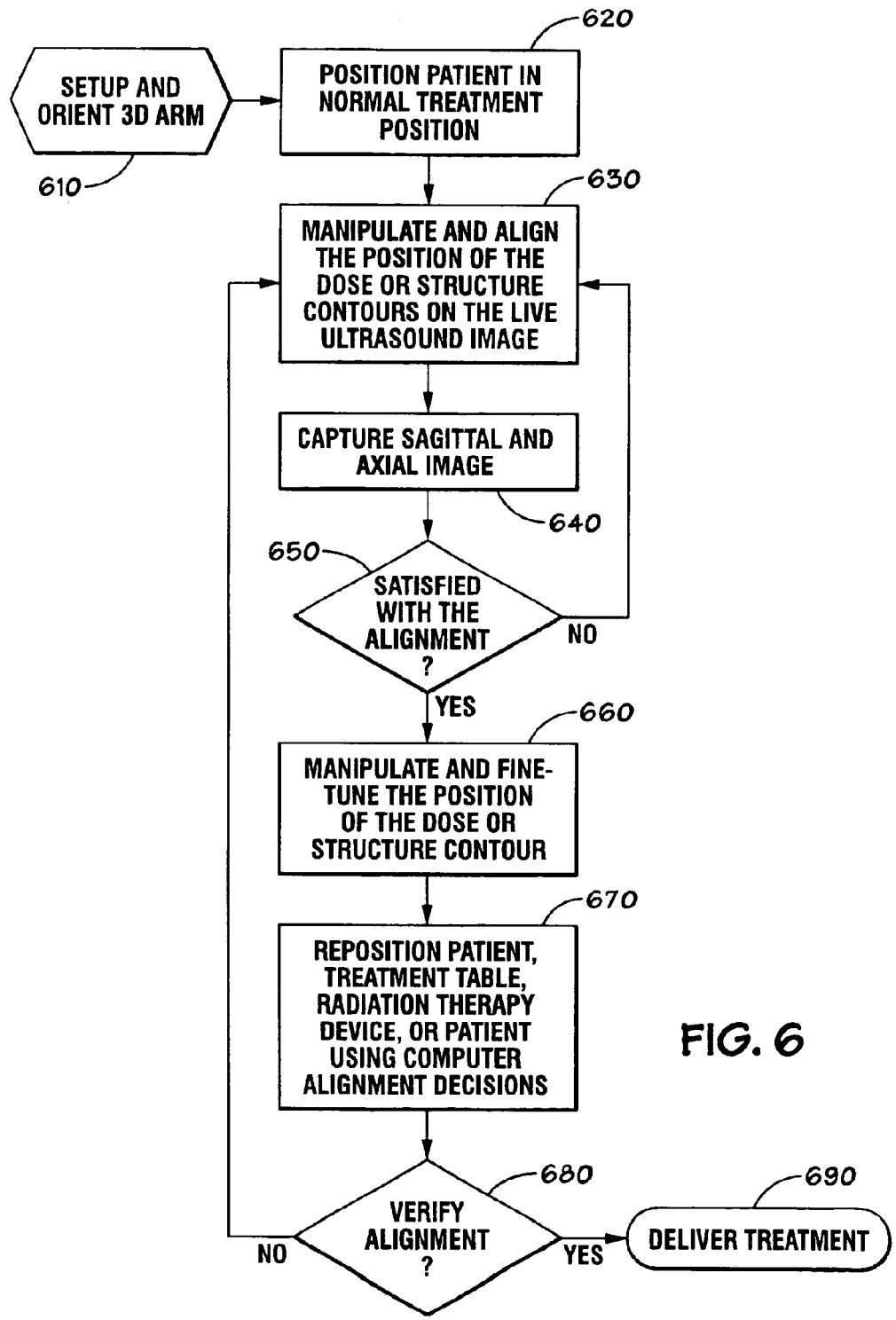
FIG. 6 is a flowchart illustrating the step-by-step method of the present invention.
Figure 7:
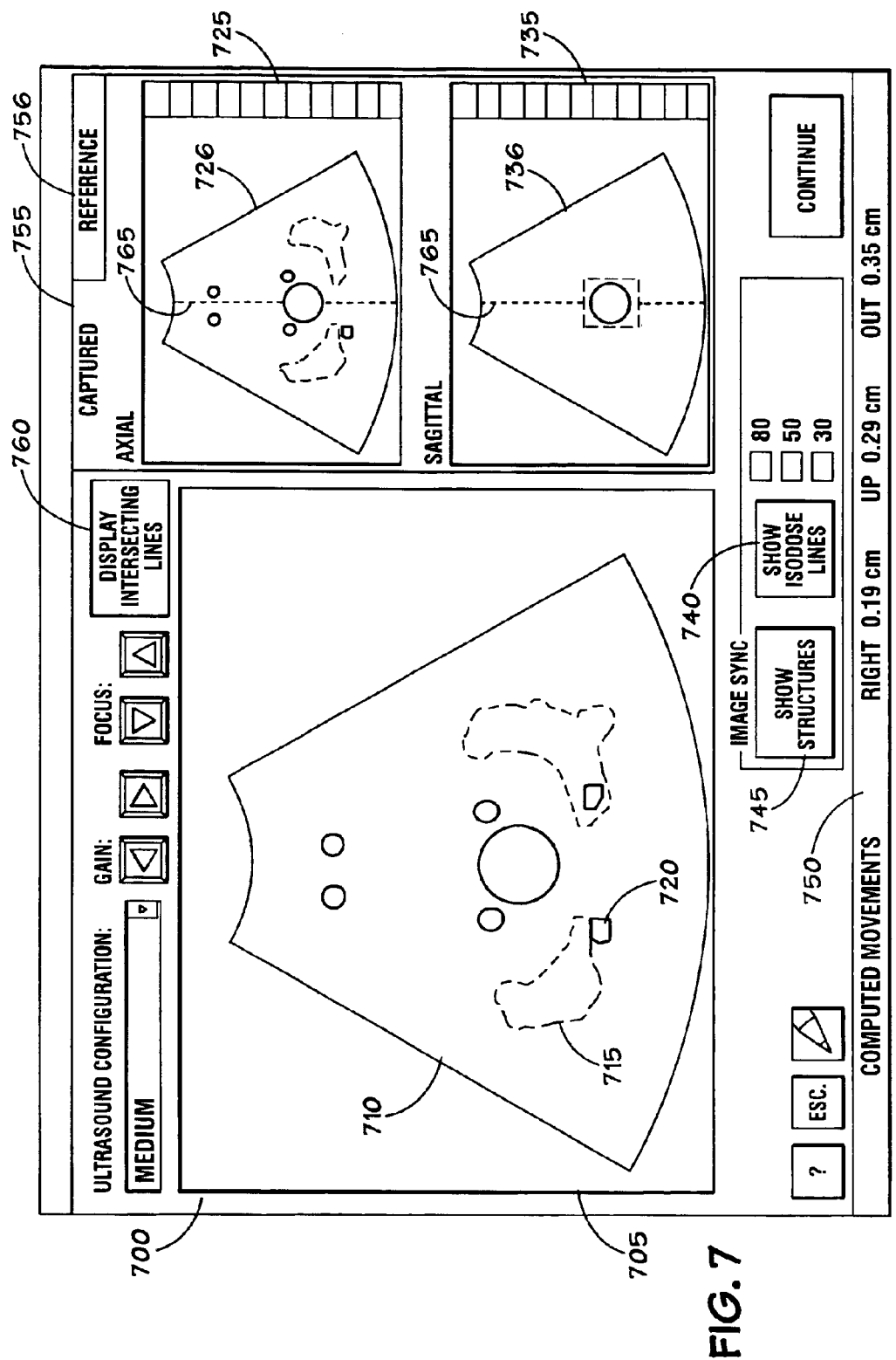
FIG. 7 is a front view of a computer screen displaying a live ultrasound image and two two-dimensional representations of treatment plan data being aligned with the live ultrasound image and two two-dimensional ultrasound images of the target, respectively, wherein the representations of treatment plan data are dose distribution and a structure contours.
Figure 8:
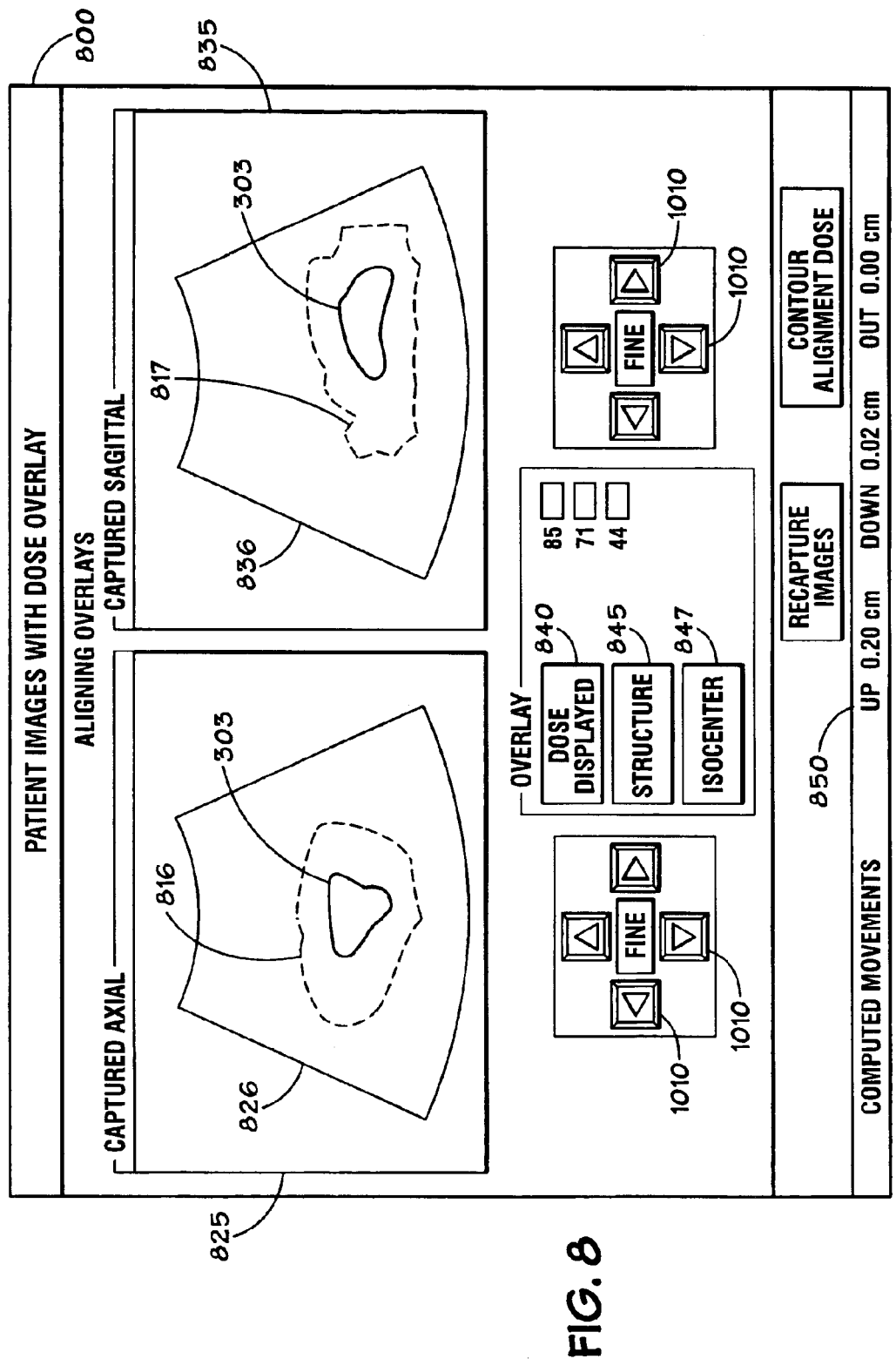
FIG. 8 is a front view of a computer screen displaying two two-dimensional representations of treatment plan data being aligned with two two-dimensional ultrasound images of the target, wherein the representations of treatment plan data are dose distribution contours.

With reference to FIGS. 6–8, the method of the present invention for aligning the position of a target 303 for use in a radiation treatment plan, which includes a live ultrasound image and at least two two-dimensional representations of treatment plan data corresponding to the target 303, will be described. As seen in FIG. 6, the first step 610 is to set up and align, or orient, the 3-D digitizer articulated arm 521 to radiation therapy device 400, in order to align the ultrasound probe 511 to the radiation therapy device 400, coordinate system. By performing this step 610, the geometric orientation, or location, of the ultrasound image generating means 510, or ultrasound probe 511, mounted to articulated arm 521 will be known with respect to the radiation therapy device 400. In turn such geometric orientation will be known for each ultrasound image to be generated. Step 610 can be accomplished by several techniques. Preferably, ultrasound probe 511, mounted upon 3-D digitizer articulated arm 521, may be releasably secured to radiation therapy device 400, as by releasably securing ultrasound probe 511 to gantry 402 or collimator 405 (FIG. 4). A receptacle, or holster, (not shown), may be attached to gantry 402 or collimator 405, and the ultrasound probe 511 may be releasably secured within the receptacle mounted on the gantry 402 or collimator 405. While the ultrasound probe 511, is received within the receptacle, the 3-D digitizer articulated arm 521 operates in a conventional manner, in combination with computer 490 and related software, to indicate where ultrasound probe 511 is geometrically disposed, or located, with respect to radiation therapy device 400. Once ultrasound probe 511 is first oriented with respect to collimator 405, when the gantry 402 is disposed in a known position, the geometric orientation, or location, of ultrasound probe 511 will always be known regardless of where ultrasound probe is located, such as in the location illustrated in FIG. 5 adjacent the patient's body 302. Another technique entails identifying at least three points on gantry 402 by touching 3-D digitizer articulated arm 521 to the points when gantry 402 is at a known position. Yet another technique for aligning 3-D digitizer articulated arm 521 to radiation therapy device 400 includes the step of registering moveable support 540, or cart 541, and the 3-D digitizer articulated arm 521 mounted thereon, to holes 543, or pins 544, on the floor 545 adjacent to treatment table 404, which holes 543 or pins 544 cooperate with the support 540, or with the wheels 542 of cart 541.

The next step 620 involves disposing, or positioning, the patient 302 in a nominal treatment position upon treatment table 404, which preferably approximates the position and orientation the patient 302 had during the imaging process. It should be noted that the set-up step 610 could alternatively follow, rather than precede, the patient positioning step 620.

The next step 630 of the method of the present invention is to manipulate the ultrasound probe 511 to display live ultrasound images 710 of the target and align the dose and/or structure contours representing the radiation treatment plan. Since it is possible to slice the overlay data, or overlay data volume slice, very quickly, a given slice of overlay data can be displayed with the associated frame of ultrasound image data. By determining the position and orientation of the ultrasound probe 511, slicing the overlay data and mixing it with the ultrasound image 710 in real time, it is possible to present to the user a display that simultaneously shows the real patient including target location and the model of the patient from the treatment planning system including isodose and structural contours. The user can see a live, or dynamic, ultrasound image 710 with the overlay data 715, 720 (representations of the radiation treatment plan) displayed on top of the live or dynamic image 710. Suitable controls such as the use of a touch activated system or use of slider controls can provide the ability for the user to shift the overlay image 715, 720, relative to the ultrasound image 710, to provide a system that enables the alignment operation, but advantageously does not require the user to disregard the dynamic aspects of the live ultrasound image 710.

In order to implement step 630, the computer 490 advantageously can display an ultrasound image capture screen 700 (FIG. 7), which displays live ultrasound images 710 of the target 303 in association with overlay data 715, 720 from the radiation treatment plan in the live ultrasound image window 705. This provides the user or operator of the target alignment system the capability of searching through two spaces simultaneously—the body of the patient, since the ultrasound probe 511 is being manipulated with respect to the actual patient as the patient lies on the table 404, and the model of the patient supplied by the treatment planning system. However, since these two spaces are by definition not aligned with each other, and perhaps they are very much misaligned, these two spaces must be aligned so that coincident slices of the actual target and representation or model of the target contain similar artifacts from the two spaces. Suitable controls, such as a touchscreen utilized in the preferred embodiment, or alternatively slider controls can provide the user the ability to make such positional shift necessary to position the overlay data 715, 720 in approximately the right alignment. The user or operator manipulates the ultrasound probe 511 and the alignment controls simultaneously. Additionally, in an embodiment, the system can allow a specific overlay structure in the live ultrasound image 710 that relates to the target 303 the operator is attempting to find, to be centered at the touch of a control button. A slider or button that controls the opacity of the overlay data 715, 720, can be provided to assist in preventing the overlay data 715, 720 from obscuring ultrasound data, or ultrasound images 710. In the touchscreen implementation, instead of repeated presses of a button, as will be described with reference to FIGS. 8–9, the user may drag the overlay data 715, 720 across the live ultrasound images window 705 in a single motion of the user's finger.

Referring still to FIG. 7, the position of the dose and structure contours 715, 720, relative to the live ultrasound images 710 may be viewed in all three windows 705, 725, 735, of the ultrasound image capture screen 700. As stated above, in performing the method of the present invention, the position of the contours 715, 720, can be moved relative to the live ultrasound image 710 as part of a user-driven "virtual alignment" process. The live ultrasound image 710 and related dose and structure contour overlays 715, 720 on the image 710 can be viewed in real time as the position and angular orientation of the probe 511 is altered by the user.

In the preferred embodiment of the present invention, the user may individually display either dose contours or structure contours through use of touchscreen buttons 740, 745, respectively. Selection of either or both buttons 740, 745, results in the display of the contours on the live ultrasound image 710 and any captured images 726, 736, in windows 725, 735, that are visible on the screen 1000. Based on the radiation treatment plan data for the patient, the system recalculates the dose and/or structure contours data such that the contours 715, 720, displayed are those for the volume slice of the radiation treatment plan that is coincident with the current (displayed) plain of the live ultrasound image 710. The overlay contour graphics are regenerated with a refresh rate of preferably at least 10 frames per second such that the overlay contours 715, 720, appear to track the features of the live ultrasound image 710 as a user adjust the position and angle of the ultrasound probe 511 relative to the anatomy of the patient.

Using the image capture window 700, the user can perform this "virtual alignment" by moving the contours 715, 720, on the live ultrasound image display 705 until they are correctly aligned to the patient anatomy as seen in the live ultrasound image 710. The system translates these contour movements into, for example, treatment table 404 or couch movements which are incorporated into the final steps of the patient alignment process, as described later. As stated, preferably the user can move the position of the contour overlays 715, 720, relative to the patient anatomy by touching the screen display anywhere within the boundaries of the live ultrasound image 710. The live ultrasound window 705 responds to these user finger "drag events" on the touchscreen by displaying the motion of the entire set of overlay dose and/or structure contours 715, 720, relative to the ultrasound image 710. The displayed contours 715, 720, are regenerated at periodic intervals such that they appear to "track" the user's finger motion as long as the finger remains in contact with the touchscreen. The displayed contours exhibit identical displacements in response to user finger drag events on the touchscreen. When the user's finger is removed from the live ultrasound image area of the touchscreen during the process of moving the contour overlays, the contours 715, 720, are frozen in a position relative to the live ultrasound image 710.

Ultimately the purpose of step 630 is to align the dose and structure contours 715, 720, for capture and storage, step 640, of at least two two-dimensional ultrasound images 726, 736, of the target 303 in the patient's body 302. If only two ultrasound images 726, 736, of the target 303 are taken, they must not be the same image. The two ultrasound images may be any two different ultrasound images of the patient 302 in the room containing the radiation therapy device, and should be as nearly perpendicular to each other as possible. Also, each image should pass through the center of the target 303 being treated.

Preferably, above each captured image window 725, 735, is an indication of a standard imaging plane, Axial or Sagittal, for example, which represents the orientation of probe 511 when the image 710 is captured. These images are generated, or acquired, when ultrasound probe 511 is disposed in the known geometrical orientation, as previously described, through operation of the position sensing system 520, or articulated arm 521. An axial image of target 303 is an image taken in a plane approximately perpendicular to the spinal cord, or longitudinal axis, of the patient 302, as well as perpendicular to the upper surface 438 of treatment table 404, as is known in the art. A sagittal image of target 303 is an image generated in a plane parallel with the longitudinal axis, or spinal cord, of patient 302, as well as being perpendicular and parallel with longitudinal axis of treatment table 404. By rotating ultrasound probe 511 with respect to the second end 522 of articulated arm 521, the desired axial and sagittal images of target 303 may be generated.

As stated previously, the radiation treatment plan can include various types of two-dimensional representations of treatment plan data, in a conventional manner, such as dose distribution contours 715, and structure contours 720, as is known in the art. The underlying radiation treatment plan data may be a three-dimensional representation of data which is converted into a two-dimensional representation, and/or two-dimensional representations of geometric information concerning radiation beam projections. The two-dimensional representations of treatment plan data can also include actual CT or MR images of the patient 302. In general, the term "treatment plan data" can include any images or data that can be used to generate, evaluate, or create, a radiation treatment plan. As shown on the upper right side of FIG. 7, an axial ultrasound image of the prostate of patient 302 is displayed and an axial dose distribution contour 716 and surrounding structures contours 721 associated with the patient's prostate in the radiation treatment plan data has been displayed and overlaid, or aligned, with a captured ultrasound image 726. Similarly, on the lower right side of FIG. 7 a sagittal ultrasound image of the patient's prostate, or target 303, has been displayed, along with the display of a sagittal dose distribution contour 717 and surrounding structures contours 722 with a captured ultrasound image 736.

After ultrasound images 726, 736, of the target 303 are taken by ultrasound probe 511 and any desired virtual alignment procedures had been completed, they may then be frozen and displayed on the captured image tab 755, preferably by touching the appropriate smaller window in the captured tab 755. At this point the computer software determines the necessary amount, type, and direction, of movement of at least one of treatment table 404, the radiation therapy device 400, or the patient 302, in order to achieve the desired location of the target 303 in the radiation treatment plan and can display such data at the bottom of the screen 700 at lower text box 750, as shown in FIG. 7. An image capture window 725, 735, may be selected multiple times, with each touch replacing the existing image with the current live image, including any available contour overlays. A reference tab 756 can provide the user reference images previously acquired for the current patient, to be used as examples of how each particular patient's anatomy appears in ultrasound images. Selecting the reference tab 756 will cause the axial and sagittal windows to display the reference images. The live ultrasound image 710 can still be captured in this mode by touching the appropriate window 725, 735. In this event the reference tab 756 is automatically switched back to the captured tab 755 and the image is stored. Any dose and structure contours that are saved with reference axial and sagittal images are retained for display on the reference tab. Additionally, any images from any alignment session can be set as the reference image.

Once the at least two images have been captured, a dashed line 765, can be displayed through the captured still images 726, 736, in windows 725, 735. This line 765 indicates where the plane of one image intersects the other. This can help locate images through the center of the anatomy of interest. This procedure is recommended for optimal alignments. The user can turn off the dashed lines 765 with the display intersecting lines button 760.

During a process of moving the contour overlays 715, 720, on the live ultrasound image 710, the removal of the user's finger from the live ultrasound image area of the touchscreen shifts the position of any contour overlays that are displayed in the captured axial or sagittal image windows 725, 735, to correspond to the static position of the contour overlays on the live ultrasound image 710. Once the final axial and sagittal images 725, 735 have been captured, any contour adjustments completed during the ultrasound image capture process are retained for use in the final steps of patient alignment as described later.

Figure 9:
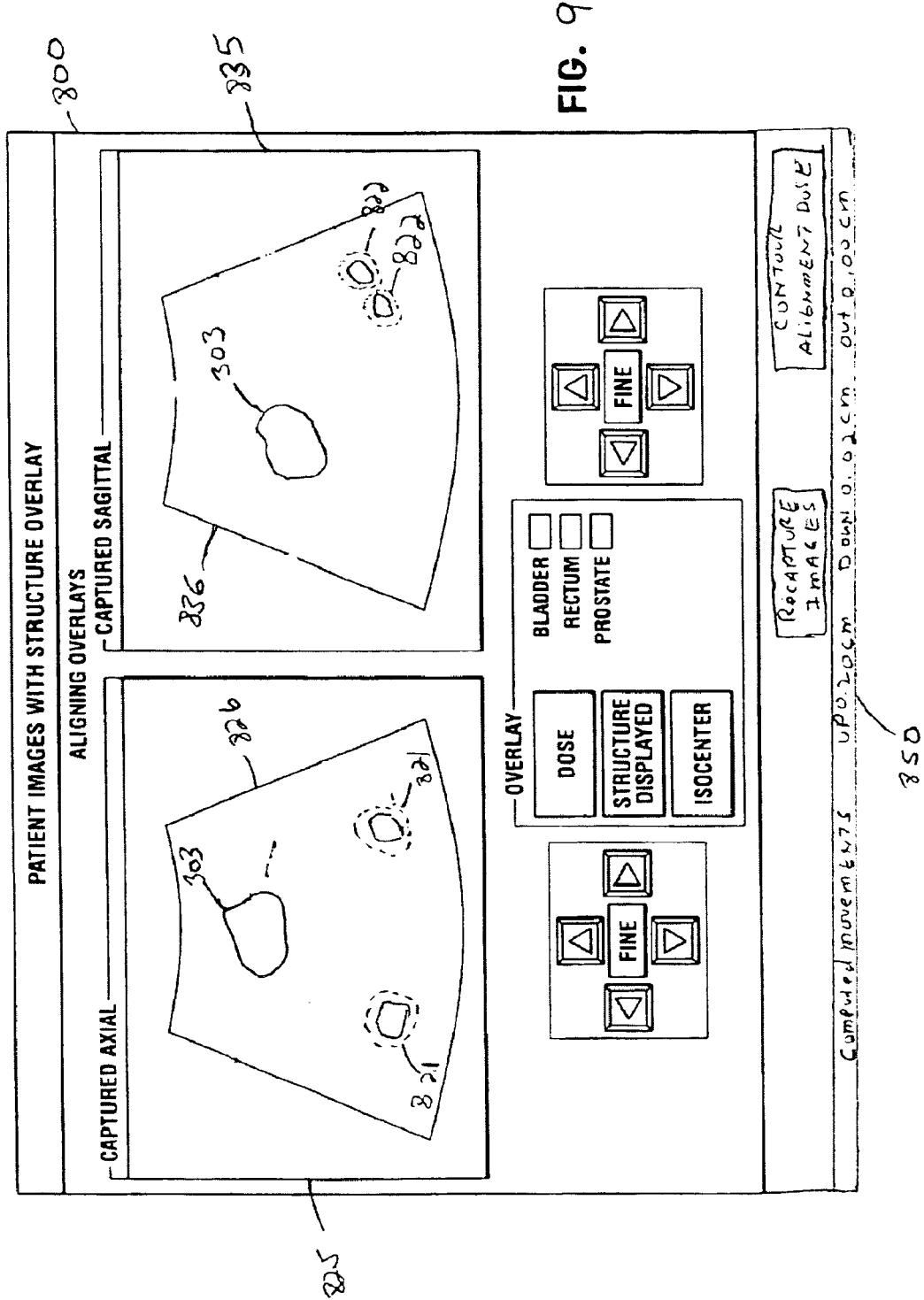
FIG. 9 is a view of a computer screen displaying two two-dimensional representations of treatment plan data being aligned with two two-dimensional ultrasound images of the target, wherein the representations of treatment plan data are structure contours.

Also referring to FIGS. 8-9, after the user determines 650 that the at least two images, such as images 725, 735 are satisfactory, the next step 660 is to re-display the captured at least two two-dimensional representations of treatment plan data corresponding to target 303 for fine-tuning of the alignment of the displayed representations of treatment plan data with respect to the displayed ultrasound images 725, 735, of the target 303 in a contour alignment window 800. In the preferred embodiment of the present invention, the user selects the continuation button 770 to exit the image capture window 700 and enter the contour alignment window 800. The contour alignment window 800 provides a larger depiction of the images displayed in the captured tab 755 of the image capture window and adds the ability to select display of the isocenter location (not shown). The window 800 provides individual selection through buttons 840, 845, 847, for display of one or more of dose contours, structure contours, and isodose position, respectively, along with the captured ultrasound images.

For example, as shown on the left side of FIG. 8, an axial still ultrasound image 826 of the prostate 303 is displayed and an axial dose distribution contour 816 associated with the patient's prostate in the radiation treatment plan data has been displayed and overlaid, or aligned, with the ultrasound image in window 825. Similarly, on the right side of FIG. 8 a sagittal ultrasound image 836 of the patient's prostate, or target 303, has been displayed, along with the display of a sagittal dose distribution contour 817 in window 835. Similarly, in FIG. 9, axial and sagittal ultrasound images, 826, 836, are displayed, with axial and sagittal structure contours 821, 822, being also displayed, and aligned with or overlaid upon the ultrasound images.

The operator, or user, of the target position verification system 500 may align, or manipulate, the representations of treatment plan data, or dose distribution contours 816, 817, or structure contours 821, 822, with respect to the ultrasound images 826, 836, using the arrow keys 1010. By manipulating, or aligning, the treatment plan data by use of arrow keys 1010 of computer 490, computer software associated with computer 490 can re-determine the amount of movement necessary to dispose the target 303, or prostate, of patient 302 with respect to the radiation therapy device 400, and to conform the location of target 303 to the desired position of the target 303 in the radiation treatment plan. As with the alignment and capture steps 630 and 640, the computer software determines the necessary amount, type, and direction of movement of the treatment table 404, the radiation therapy device 400, and/or the patient 302, in order to achieve the desired location of the target 303 in the radiation treatment plan. The arrow keys 1010 are by default defined for the couch, or treatment table, 404 motion directions of up, down, in, out, right, and left, and the output of that process is the set of offsets in treatment table position required to realize the desired positioning of the target 303 in the radiation treatment plan. Note, this step further allows real-time correlation, display, and alignment of target 303 with patient 302 coordinate system and two-dimensional representations of treatment plan data from the radiation treatment plan whether or not alignment in the image capture window 700 was previously accomplished. Also note, a reference tab (not shown) similar to tab 756 (FIG. 7) can also provide reference images.

By utilizing at least two ultrasound images not being the same image, the computer software can determine the necessary set of offsets in three dimensions as previously described. It should be noted that if only one ultrasound image is utilized, the computer software could determine a set of two dimensional offsets which could be useful in some medical applications, including some radiation treatment plans.

Still with reference to FIG. 6, the next step 670 is to reposition, or move, the treatment table, or couch, 404, the gantry 402 and/or collimator 405, or patient 302 according to the necessary amount, type, and direction, of movement of the treatment table 404, gantry 402 and/or collimator 405, determined by computer 490, in order to conform the desired position of target 303 in the radiation treatment plan. If desired, the patient's body 302 may also be repositioned to achieve proper rotational and/or tilt alignment.

The next step 680 is to verify the alignment, or position, of the target 303, as by repeating steps 660 to 670 or 630 to 670, if necessary. Once treatment table 404 has been repositioned, the system 500 is used again in real-time mode to verify proper alignment at the new treatment table 404 position. The operator repeats step 640 by selecting the recapture images button 860 to see whether the dose distribution and structure contours, or two-dimensional representations of treatment plan data, align with the ultrasound images. If the images and the contours, or two-dimensional representations of treatment plan data, do not align, steps 630 to 670 may be repeated. Alternatively only steps 660 to 670 may be repeated until the desired position of the target 303 has been obtained.

At that point in time, the next step 690, will be to deliver the desired radiation treatment. The method of the present invention may also include the step of storing the treatment plan data, representations of treatment plan data, and ultrasound images, for use in future procedures, which would include patient set-up, operator verification, physician review, and/or patient records purposes. The method and system 500 of the present invention may also include the utilization and providing of a digital camera (not shown) to take a picture of the patient 302 while on treatment table 404 to record the patient's identity, equipment set-up, and patient orientation, which can be stored in computer 490 for future use.

It is to be understood that the invention is not to be limited to the exact details of construction, operation, exact materials, or embodiments shown and described, as obvious modifications and equivalents will be apparent to one skilled in the art. For example, the method and system of the present invention could be used for patient contour position validation and dosimeter placement for delivery validation using anthropomorphic phantoms. With the ultrasound probe removed from the articulated arm, the arm may be aligned to the gantry coordinate system, and can then be used to provide dose, structure, and contour information from the treatment planning system for the point at the end of the arm. Accordingly, the invention is therefore to be limited only by the scope of the appended claims.

What is claimed is:

1. A target alignment system for use by a user with a radiation therapy device and a radiation treatment plan for treating a target within a body of a patient and for aligning a position of the target within the body of the patient to a predetermined position used in the development of the radiation treatment plan, comprising:

an ultrasound probe for generating live ultrasound images of the target;

a position sensing system for indicating the position of the ultrasound probe with respect to the radiation therapy device, adapted to provide a reference location of the target with respect to the radiation therapy device;

a computer system including a computer having memory and a monitor with a screen associated therewith, a radiation treatment plan stored in the memory, the computer responsive to the position sensing system and ultrasound probe, and adapted to:

display on the monitor screen the live ultrasound images of the target in association with representations of the radiation treatment plan;

align the displayed representations of the radiation treatment plan with the displayed live ultrasound images in response to a user input;

capture and store at least two two-dimensional ultrasound images of the target overlaid with the aligned representations of the treatment plan data, the ultrasound probe being disposed in a different geometric orientation for each captured ultrasound image; and determine, in response to the alignment, the difference between the location of the target in the ultrasound images and the location of the target in the representations of the radiation treatment plan.

2. The system of claim 1, wherein the displayed representations of treatment plan data include at least one of an isodose distribution contour and a structure contour.

3. The system of claim 1, wherein the at least two two-dimensional ultrasound images include an axial image and a sagittal image.

4. The system of claim 2, wherein the computer is adapted to display features of the live ultrasound image overlaid with associated dose and structure contour data as the user adjusts the position and angle of the ultrasound probe relative to a patient anatomy.

5. The system of claim 4, wherein the computer is adapted to recalculate dose and structure contour data such that the contours displayed are for a volume slice of radiation treatment plan data that is coincident with a current plane of the live ultrasound image.

6. The system of claim 2, wherein the computer is responsive to the user input and adapted to move a displayed position of the contours relative to the live ultrasound image as part of a user-driven virtual alignment.

7. The system of claim 6, wherein the computer system includes a user input device in the form of a touchscreen, and wherein in response to a user finger drag event, the displayed contours exhibit identical spatial displacements relative to each other.

8. The system of claim 6, wherein the computer is adapted to respond to the user touching a monitor screen display anywhere within boundaries of the live ultrasound image displayed on the monitor screen and dragging a user finger in a desired direction to move the position of the contours relative to the live ultrasound image.

9. The system of claim 7, wherein the computer is further adapted to regenerate displayed contours at periodic intervals such that they appear to track the motion of the user finger.

10. The system of claim 1, wherein the computer is further adapted to display on the monitor screen prior captured and saved two-dimensional ultrasound images of the target defined as reference images, the images overlaid with associated representations of the radiation treatment plan.

11. The system of claim 1, wherein the position sensing system includes the 3-D digitizer articulated arm.

12. The system of claim 1, wherein the computer is further adapted to display an image capture screen having a live ultrasound image window for displaying a live ultrasound image overlaid with position adjustable representations of the radiation treatment plan, the position of the representations of the radiation treatment plan displayed relative to a current plane of the displayed live ultrasound image for performing a user alignment of the displayed representations of the radiation treatment plan with respect to the displayed live ultrasound image, and at least two other static image windows displaying at least two captured two-dimensional ultrasound images of the target overlaid with the corresponding aligned representations of the radiation treatment plan.

13. A method of aligning the position of a target within a body of a patient to a predetermined position used in the development of a radiation treatment plan for the patient, comprising the steps of:

(a) disposing the patient on a treatment table of a radiation therapy device;

(b) providing an ultrasound probe;

(c) manipulating the ultrasound probe to display live ultrasound images of the target, and displaying spatially associated representations of the radiation treatment plan overlaid upon the live ultrasound image;

(d) aligning the displayed representations of the radiation treatment plan with the displayed live ultrasound images;

(e) capturing at least two two-dimensional ultrasound images of the target in the patient's body overlaid with the aligned representations of the radiation treatment plan data, the ultrasound probe being disposed in a different geometric orientation for each captured ultrasound image; and (f) determining an amount, and type, of movement of at least one of the treatment table, the radiation therapy device, and the patient required to position the target to conform the current position of the target to the position of the target used in the development of the radiation treatment plan.

14. The method of claim 13, wherein the displayed representations of radiation treatment plan includes at least one of an isodose distribution contour and a structure contour.

15. The method of claim 13, wherein the at least two two-dimensional ultrasound images include an axial image and a sagittal image.

16. The method of claim 14, including the step of tracking features of the live ultrasound image overlaid with associated dose and structure contour data as a user adjusts the position and angle of the ultrasound probe relative to a patient anatomy.

17. The method of claim 16, including the step of recalculating dose and structure contour data such that the contours displayed are for the volume slice of the radiation treatment plan that is coincident with the current plane of the live ultrasound image.

18. The method of claim 14, including the step of performing a virtual alignment by moving the contours overlaid on the live ultrasound image device until they are correctly aligned to the patient anatomy as viewed with respect to the live ultrasound image.

19. The method of claim 16, including the step of moving the position of the contours relative to the live ultrasound image as part of a user-driven virtual alignment.

20. The method of claim 18, wherein all displayed contours exhibit identical displacements relative to each other in response to a user finger drag event.

21. The method of claim 14, wherein the step of aligning the displayed representations of the radiation treatment plan is accomplished by touching a monitor screen display anywhere within the boundaries of the live ultrasound image and dragging a finger in a desired direction.

22. The method of claim 20, including the step of regenerating at periodic intervals contours displayed and overlaid upon the live ultrasound image, such that movement of the contours appears to track the motion of the finger.

23. The method of claim 22, wherein the step of regenerating contours includes refreshing the live ultrasound image and associated overlaid contours displayed on the monitor at a rate of at least ten frames per second.

24. The method of claim 13, including the step of mounting the ultrasound probe to a 3-D digitizer articulated arm.

25. The method of claim 13, including repeating steps (c) through (f).

* * * * *